: (12) United States Patent
Schuler et al.

(10) Patent No.: US 8,315,712 B2
(45) Date of Patent: *Nov. 20, 2012

(54) HYBRID SCIENTIFIC COMPUTER SYSTEM FOR PROCESSING CANCER CELL SIGNALS AS MEDICAL THERAPY

(75) Inventors: Eleanor L. Schuler, Rio Rancho, NM (US); Donald E. Nash, Albuquerque, NM (US); James K. Poliner, Rio Rancho, NM (US)

(73) Assignee: Neuro Code Tech Holdings, LLC, Albuquerque, NM (US)

(*) Notice: Subject to any disclaimer, the term of this patent is extended or adjusted under 35 U.S.C. 154(b) by 0 days.

This patent is subject to a terminal disclaimer.

(21) Appl. No.: 12/936,791

(22) PCT Filed: Apr. 17, 2009

(86) PCT No.: PCT/US2009/040901
§ 371 (c)(1),
(2), (4) Date: Oct. 28, 2010

(87) PCT Pub. No.: WO2009/129434
PCT Pub. Date: Oct. 22, 2009

(65) Prior Publication Data
US 2011/0130754 A1    Jun. 2, 2011

Related U.S. Application Data

(60) Provisional application No. 61/045,667, filed on Apr. 17, 2008.

(51) Int. Cl.
*A61B 18/12* (2006.01)

(52) U.S. Cl. ............................................. 607/72; 607/2
(58) Field of Classification Search ................... 607/72, 607/2
See application file for complete search history.

(56) References Cited

U.S. PATENT DOCUMENTS

| | | | |
|---|---|---|---|
| 6,575,969 B1 * | 6/2003 | Rittman et al. | 606/41 |
| 7,010,356 B2 * | 3/2006 | Jog et al. | 607/116 |
| 2001/0051766 A1 * | 12/2001 | Gazdzinski | 600/309 |
| 2004/0176804 A1 * | 9/2004 | Palti | 607/2 |
| 2005/0222646 A1 * | 10/2005 | Kroll et al. | 607/72 |
| 2007/0187840 A1 * | 8/2007 | Dell'Acqua-Bellavitis et al. | 257/784 |

* cited by examiner

*Primary Examiner* — Carl H Layno
*Assistant Examiner* — Jennifer Ghand
(74) *Attorney, Agent, or Firm* — Barnes & Thornburg LLP

(57) ABSTRACT

A hybrid scientific computer system with processor capable of recording, storing and reprogramming the natural electrical signals of cancer cells as found in tumors of humans and animals. The reprogramming process is designed to create a confounding electrical signal for retransmission into a malignant tumor to damage or shut-down the cellular internal electrical communication system. Altering the electrical charge on the glycocalyx of the outer cell membrane is also part of the treatment by application of ions. Confounding electrical signals are stored in a scientific cancer cell signal processor of the computer system. The invention causes cancer cell death as a medical treatment using ultra-low voltage and amperage encoded signals which are re-programmed from cancer cell communication signals.

20 Claims, 1 Drawing Sheet

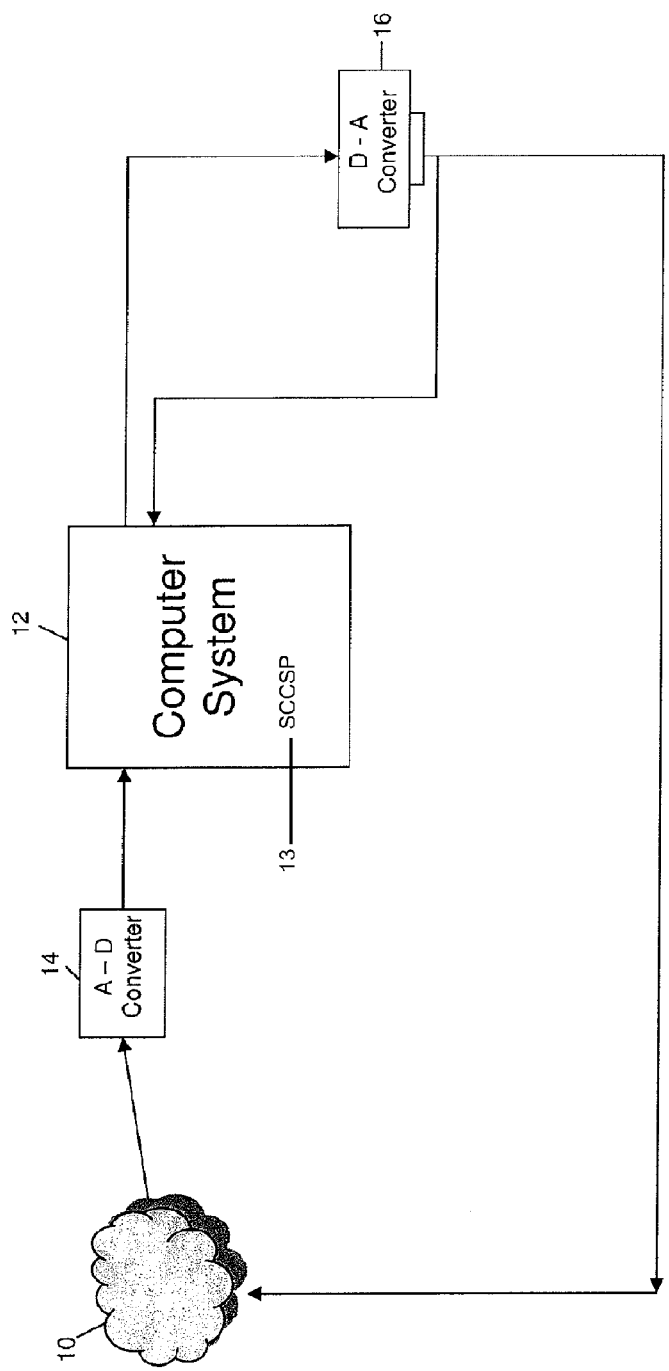
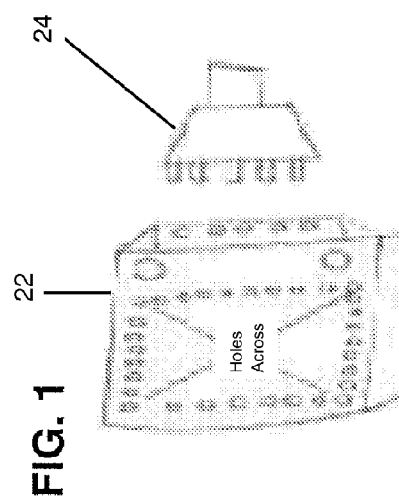
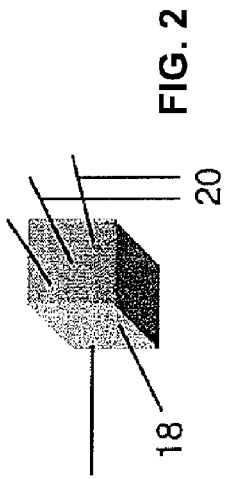
FIG. 1
FIG. 2
FIG. 3

HYBRID SCIENTIFIC COMPUTER SYSTEM FOR PROCESSING CANCER CELL SIGNALS AS MEDICAL THERAPY

RELATED APPLICATION

This application claims priority to U.S. Provisional Application No. 61/045,667, filed Apr. 17, 2008.

BACKGROUND OF THE INVENTION

The present invention relates to the medical therapy of cancers throughout the entire human or animal body. More particularly, the invention relates to an all analog computer system or a hybrid analog-digital computer system for receiving and recording the intrinsic electrical signals of individual cancer cells or the electrical signature of clusters of malignant cancer cells. The signals are recorded and entered into the computer system for analysis and reprogramming to treatment signals. The treatment signals are then transmitted or broadcast into malignant tumors as a means to shut down or damage the cellular-based electrical system to destroy the cancer.

This invention is an improvement of the invention disclosed in co-pending International Application No. PCT/US2009/030701, filed Jan. 12, 2009, the disclosure of which is incorporated herein by reference.

Every living organism is made up of cells, which are the lowest level of structure capable of performing all the activities of life. All cells, including cancer cells, arise from preexisting cells. Cancer is a very complicated disease. It's not just one type of disease, so it's hard to figure out and then devise a treatment program for state-of-the-art approaches. Cancer is a disease where cells undergo cancerization and they then reproduce relentlessly. Cancer cells are still the same as normal cells in many ways, but they behave differently and have adapted new communication tactics. Conventional treatment of cancer is a problem, because if one uses medications that are quite toxic, that often injures normal cells, too. Thus, a better way to treat cancer is to use a tactic(s) that does not impact or minimizes injury to healthy cells. Therefore, being able to pinpoint cancer cells through their electrical and/or audio signals is critical.

Every biological process is also an electrical process. All living cells, including cancer cells, have electrical capability and can communicate internally to operate processes within the cell as well as coordinate with adjacent cells. Many different cells are able to participate in long distance communication both within and outside the body. Modern neurosciences, cell biology and microscopy along with medical sciences specialties have steadily examined the anatomy and physiological characteristics of healthy and cancerous cells.

Normal cells have electro-chemical processes within their surrounding plasma membranes, which are the outer limit of the cell proper. Within their individual plasma membranes are links to the internal cell which consists of processes that operate the electro-chemical mechanisms that allow cell functions to be maintained. Cells have to obtain nutrition and be able to reproduce, defend and repair themselves as well as perform the primary purpose for which they are designed.

There are many kinds of cells, each specialized to fulfill specific duties and functions. Cells are small—a pencil dot might be the space occupied by 60 to 500 cells. Cancer cells can exist as small-cell or large-cell varieties and can form tumors of great variation in size. Normal cells are of different sizes depending on the kind of mechanisms that are enclosed within their plasma membrane so as to allow enough cellular space for them to perform their intended duties. All cells require a blood supply to deliver nutriments and oxygen. Many cells exhibit nerve connections to allow communication capability within multi-cellular organisms. Certain cells are able to chatter or signal among themselves and send messages to adjacent and even distant cells to coordinate operational requirements concerned with body or even tumor homeostasis.

Like all biological mechanisms, cells have some sort of electrical and sometimes audio signaling process and connections and means to communicate with other cells. Certain cells are connected to adjacent cells of similar type and purpose to allow coordination of their duties and efforts. At the borders of demarcation between different types and families of normal cells there may be signals that maintain separation and cooperation so as not to interfere with each others duties and operations. Clusters of cells which make up a functioning organ, muscle, sensor or gland are constructed of a variety of cells that together cover all the functions that are required, including sensory and communication capability.

Cells produce natural, rapid, low voltage, low amperage signals that are discrete and localized. Cellular signals that need to travel long distances use a relay tactic which enlists the cooperation of other cells to help transmit an accurate signal. Most if not all the tiny electrical pulses and codes produced within a cell draws their energy from a specialized chemical or electrochemical process that resides within their surrounding plasma membrane wall and/or within the internal cell itself. The signals are formed from the most fundamental bits of electricity first produced by prehistorically primitive examples of single cell life.

Recently there have been discoveries of sophisticated cellular communication systems over the entire being including cell to cell and from cellular system to other cellular systems. Cancer cell communications are distinguishable from healthy cells. Cells have had to have a way to transfer signals not only between adjacent cells but inside the cells themselves to operate their own individual metabolisms and repair operations. To do that a cell utilizes chemicals and ions of sodium, potassium, magnesium and calcium to generate an electrical signal; so chemical processes begot electrical signaling. The signal shape, amplitude and frequency create the communication encodement system for all kinds of cells that operate everything within the human body. Less sophisticated but similar cellular communication systems are found in the lesser order animals and even single celled microbes.

Cells are attached to one another to both maintain structural integrity and to facilitate communication between cells. Some sort of cytoskeleton provides cellular shape and strength to every cell. Connections through the cell walls serve as structural methods to both attach to adjacent cells and to allow communication between those connected cells. The operative connections between cells can take several forms. They can be laced together with fibrous strands, gap junctions or ion channel ports which are riveted together. Additionally, other tactics for joining cells exist as tight junctional contacts. It is the objective of cells to have communication mechanisms between all cell walls that touch neighboring or adjacent cells of like-type cells. Otherwise, when a border exists between entirely diverse cell types there may be little communication. Instead the diverse cellular based vital-organs, glands or muscles operate via two-way nerve networks to and from the brain for exchange of information and coordination of all activity. Neuron signal sets are stored in brain structures such as the medulla oblongata to serve as readily available information for body homeostasis. Nerves and strings of neurons within nerves provide communication between organs, muscles, glands and sensors and other multi-cellular clusters that are part of the larger multi-cellular species of animalia.

It is not common knowledge that many cells are involved in receiving electronically formatted or audio communications and also can send answering signals themselves. However, those that understand that there is cellular signaling believe that most of it is done chemically, and perhaps only within the cell itself. Most people acknowledge that there is electrical signaling in the brain. They believe that there is a great amount of signaling between many brain structures. Usually those who advance into neuro-science studies recognize that nerve communication is at work where neurons are involved, but they will likely only partially understand that mechanism. On the other hand, neuroscientists have experience in recording nerve signaling but do not store the signals in a scientific computer system where it would be available for re-transmission to be useful as treatment for diseases.

Cells have electrical capability and can communicate at a minimum within a single cell or a small group of similar cells. Functional cell clusters have erected a network for sending signals among themselves. Cell clusters that make up functional systems are also connected to nerves that both bring information from the brain and send status information to the brain.

There are no medical technologies in commercial use today that record, store, reprogram and transmit ultra-low voltage cellular signals that could affect cellular electrical communication and its associated performance.

Living cancer cells also have a rigorous communication system and a method to generate an outer membrane electrical charge as part of their camouflage from attack by the human or animal immune system. They have many characteristics that predominate in normal non-malignant cells of every type, especially having to do with metabolic processes.

Defective chromosomal and genetic forces which are inherited do a lot of mischief and severely threaten life and account for much of cancer's morbidity and mortality. Unfortunately, present day medical treatments, as remarkably successful as they are, are simply not always good enough. Part of the practical problem is that it is difficult to detect most early stage malignancies. When cancer is eventually recognized it may have extended into nearby tissues, bones, blood vessels, lymphoid systems and organs in an unpleasant metastasis process. Many cancer patients don't come to the clinician's office until serious detectable symptoms are present. Physical examination, history taking and X-ray and CT scan often provide the initial information and clues as to the location and staging of a potential malignant disease. Further evaluation can be by exploratory surgery, MRI, MRA and PET scans. A biopsy to collect a sample of a suspected tumor and microscopic studies by a pathologist is utilized to identify the species and to grade and stage any cancer cells. Today there is a major quest to identify all cancer sites and plan a treatment regime. Present-day treatments largely embrace surgery, radiation and chemotherapy.

Cancer cells may exhibit different impedance and electrical membrane potential than healthy cells. The malignant cell has higher levels of sodium which contributes to the electrochemical ability to generate internal signals. Cellular electrical abnormalities likely may be the basis of the rapid cancer reproduction and the root of its aggressiveness. Likely both the plasma membrane charge and the internal electrical metabolic and reproductive signaling carry the instructions that drive the relentless spread of cancer clusters. The cancer cell features a well established electrical constant which is unlike healthy cells. Therefore a tactic that would alter the tissue electrical encodement of a cancer cluster is expected to interfere with the internal metabolic process and reproduction, as well as its resistance to attack by the immune system. This electrical characteristic is dependent on electrophilic compounds associated with the cell membrane wall and the availability of ions and electromagnetic forces in the extra cellular spaces around the cell. Additionally, the water content, oxygen levels, minerals, pH, and the organization of the plasma membrane all interplay with the way the cancer signals.

Ruination of the electrical and audio signaling properties of the cell can be expected to prevent mitosis, disturb metabolic processes, scramble cell communication to adjacent cancer cells, damage the internal processes that use oxygen, glucose, potassium, sodium, calcium, magnesium and finally disturb the transport of anticipated nutrients to the cell interior. Finally, the loss of its electrical system will no doubt harm at least some of the electrochemical and strict chemical reactions that occur within the individual cancer. The invention's interclusio and mortifier treatment signals cascade the tumor toward catastrophic cellular systems failure.

SUMMARY OF THE INVENTION

The invention provides a system for treating cancer by causing apoptosis. The invention includes a computer system comprising a processor for modifying a resident electrical signal found in a specie of cancer to form at least one confounding electrical signal unique to each resident electrical signal and a data storage for all confounding electrical signals. A probe is provided for applying a selected one of the confounding electrical signals to the cancer to cause apoptosis.

In accordance with the preferred form of the invention, the probe is an imulus. The imulus preferably comprises a plurality of nanotubes arranged in a brush-like fashion.

The computer system includes a hybrid analog computer for providing information to the computer system. The invention also includes a probe for determining the resident electrical signal found in a specie of cancer. Preferably, the probe includes at least one microphone for also determining audio signals of the cancer.

BRIEF DESCRIPTION OF THE DRAWINGS

The invention is described in greater detail in the following description of examples embodying the best mode of the invention, taken in conjunction with the drawing figures, in which:

FIG. 1 is a schematic illustration of the system according to the invention for determining a resonant electrical signal found in cancer, creating a confounding electrical signal, and applying the signal to the cancer, FIG. 2 is a schematic illustration of an imulus treatment tip or probe having a plurality of nanotubes or nanowires, and FIG. 3 is a schematic illustration of an imulus treatment tip or probe comprising a plurality of nanotubes or nanowires, and used primarily for treatment purposes.

DESCRIPTION OF EXAMPLES EMBODYING THE BEST MODE OF THE INVENTION

The invention is directed toward a system for creating a cancer signal technology, i.e., the processing of cancer cell electrical signals for medical therapy of cancer diseases. Most particularly, the invention includes a hybrid data acquisition, monitoring and control system referred to as the hybrid scientific computer system. The hybrid scientific computer system features an assemblage of hardware and software components for monitoring, analysis support, recording and archiving data, and controlling the treatment of cancer cells. The invention is directed to the intrinsic electrical and audio signals, defined as the communication signals of cells and the electrical signature of cancer cells and clusters of malignant cancer cells. An integral component of the hybrid scientific computer system assemblage is the imulus treatment tip and a computer component integrated with electrical assemblages defined as the scientific cancer cell signal processor. Cell communication signals are entered into the hybrid scientific computer system, via the imulus treatment tip, for monitoring and display, analysis, storing and reprogramming into treatment signals. The treatment signals are transmitted back into the malignant cancer cells or tumor malignancies via an imulus treatment tip as a means to shut down or damage the cellular-based electrical system with a goal toward destroying the malignancy.

The invention provides a system for processing of cancer cell electrical signals for medical therapy of cancer. The invention encompasses a hybrid scientific computer system for monitoring, data acquisition and controlling the treatment method to kill cancer cells by interfering-with or shutting-off individual malignant cellular electrical and communication systems through the imulus treatment tip and scientific cancer cell signal processor. One aspect of a treatment option is designed to interfere and reverse the cell wall glycocalyx electrical charge from negative to positive by injecting ions of potassium, sodium, magnesium or calcium by means of the imulus treatment tip. On the other hand if it is desired to alter the glycocalyx so that it is more negative the ions of chlorides, sulfates or phosphates may be used as an optional treatment.

The treatment commences by recording the electrical/audio signals of a cancer cell or group of cancer cells through the imulus treatment tip and storing such signals in the scientific cancer cell signal processor. Such cancer cell signals are evaluated and altered by reprogramming within the scientific cancer cell signal processor to confound the electrical cellular apparatus when the codes are re-transmitted into the cancer cell or cluster back through the imulus treatment tip.

In accordance with the above stated objectives the hybrid scientific computer system is used to acquire, display, support analysis, record and store within a computer processor the resident electrical/audio signals of cancer cells. The cellular signals are analog in nature and are reprogrammed within the processor to serve as confounding signals and are then are saved in memory for later re-transmitting into the same or similar cancer cells as medical therapy. The goal is to shut down or damage the natural electrical signals of cancer cells so as to cause cell death.

A cancer cell cluster or tumor is illustrated at 10 in FIG. 1. By means of an imulus or other probe, the resident electrical signal or signals of the cancer are then provided to a computer system 12 for storing and processing. Typically, the computer system 12 is digital, and in order to accept the electrical signals from the tumor 10, an analog to digital converter 14 is used. If the computer system 12 employed includes an embedded analog to digital converter, the converter 14 can be omitted.

It is the computer system 12 in which all of the processing, analysis and generation of confounding electrical signals occurs. In order to treat the tumor 10, the confounding electrical signals are applied directly to the tumor 10 via an imulus or probe after conversion to analog state by a digital to analog converter 16.

The technical approach is to initially develop a number of cancer cell resident electrical signals for different species of cancer and perfect reprogrammed confounding type signals. The user then sorts and reprograms the natural signals of the cancer cell and tinkers with the electrical signatures and coding to finally select appropriate treatment electrical signals, also known as confounding electrical signals. This is followed by devising a library/data-base of treatment signals. The collection of treatment signals may be cataloged as to the species of cancer and anatomical location and are located in the scientific cancer cell signal processor (SCCSP) 13. During treatment of a cancer the first step is to identify the species of cancer and then select the proper confounding signal with which treatment will begin. Once the treatment team knows the species such as carcinoma or sarcoma they select from the computerized library/data-base the most appropriate treatment signal. There are approximately about a total of 200 cancer species in existence. Ultimately the treatment library will be composed of at least as many definitive cancer confounding, interclusio or mortifier signals. Carcinoma species is the most common cancer and likely represents something like 50% of all potentially cancerous tumors found throughout the body.

Once the cancer cell locations in a patient have been identified, the cancer cellular electrical activity has been recorded and analyzed, and an appropriate response has been determined, the medical staff can develop and initiate a treatment protocol. The protocol will follow established medical procedures with the main objective of applying the proper signals and appropriate electrical energy to the cancerous cells to cause apoptosis. The computer system 12 contains a low voltage and amperage power supply to ensure the correct voltage and amperage is delivered to the cancerous cells. The electrical energy delivered is less than 1 volt and less than 10 millionths of an amp for a pulsed application on the cancer over a few seconds. The treatment may be repeated. The range of electrical treatment may span upwards of 2 volts and 70 micro amps and as low as one-tenth of a volt or possibly even lower at 2 microamps or even lower into the picoamp range. The treatment time may extend up to 4 minutes or more and is repeatable over days if required. The treatment signals in the form of an electrical signal will have a definable shape and be encoded to confound the natural electrical activity found in the cancer cell plasma membrane wall and within the very interior of the cell proper. With the use of the proper code to shut off cellular electricity, the result is apoptosis of the cancer. Cancer death can begin in less than an hour once its metabolic processes are shut-down. Cell death actually may occur in less than 10 minutes as human brain cells do when blood circulation or electrical signals are turned off. Natural resuscitation of the cancer cell may be possible if the confounding electrical signal treatment is too brief or incomplete. Otherwise, irreversible biological decay will set in as long as the cellular process has been severely damaged by the treatment signals. The body immune system is expected to consume the dead or dying cancer as soon as the outer cell membrane negative electric charge is off or markedly diminished. It is the strong negative outer electrical charge of the cancer cell membrane glycocalyx that keeps the immune cells from attacking since they too are negatively charged and would be repelled from one another. Normal cells have outer coat charges that are usually positive and are therefore accessible to the negatively charged immune system cells.

Treatment is done with a small cable of total diameter no more than a wooden match stick. The imulus or treatment contact unit 18, as shown schematically in FIG. 2, is small but contains hundreds or thousands of carbon nanotubes 20. The nanotubes may be hollow or partitioned. In addition they may be coated with a metal deposition, or chemical that interferes with the glycocalyx strong negative electrical charge. The carbon nonotubes equipped imulus 18 will appear under a microscope like a hair brush. Each nano fiber tube is about one-ten-thousandths of a human hair in diameter. The imulus 18 can be used to both record and apply the treatment signal and may be of different sizes to fit the various cancer clusters. The physical approach to the cancer can be guided by fluoroscopy or other visualization apparatus or system to insure that the treatment is applied properly and completely and is directed at the correct target.

The imulus 18 is positioned to make contact with the tumor as the primary junction between the computer system 12 and the malignant cellular tumor 10 which is to be treated. Some modified nano carbon tubes may also act like an antenna and only need to be in close proximity of the malignancy to send in the interclusio or impulses mortifier codes. Insertable links, implantable antennas and contact pads or implacable treatment needles of carbon or metal can be in the arsenal of imulus attachments, among others.

It is preferred that analog computers are used that are as sensitive and able to record the cancer electrical signals as required. As analog computer developments advance they may be more suitable and be the system of choice in destroying cancer cell life. Otherwise the system as illustrated can utilize A-D and D-A converters 14, 16 interfaced with a digital processor in the computer system 12 using appropriate software to control confounding signals.

The main treatment quest consists of locating all of the cancer islands and clusters for treatment. Signals to shut down the cancer must affect every malignant cell at a given site. Communication can travel through portions or layers of tumor cells, traveling from cell to cell. Therefore moving the imulus around the tumor 10 will be necessary to make certain that every cellular communication system present within the malignancy is disabled or destroyed.

While the preferred signal handling system embodiment to destroy cancer cells is a full analog technology, the current state of computer systems is not able to deliver such a scientific computer that would work at the extremely ultra-low voltages and at the speed required to capture and record the natural signals of cancers. Therefore FIG. 1 outlines the requirements for a hybrid system to process cancer treatment codes. The system of the invention uses a hybrid analog/digital computerized system which requires at its entry an A-D converter 14 of high sensitivity to record the exclusively analog cellular signals of cancers. Secondly, the signal has to be transferred into the scientific cancer cell signal processor 13 in the computer system 12 where it can be stored and reprogrammed to confound the natural cellular signals and control any power supply required.

The computer system 12 includes several components. First, it must have a typical laptop or desktop computer for control, data acquisition, programming and application of treatment. It must allow for storage of ambient and environmental signals as well as potentially interfering biological noise so that the treatment or confounding electrical signals can be as pure as possible. LabVIEW Graphical Software provided by National Instruments Corporation of Austin, Tex. is particularly suitable for handling the graphical aspects of the invention. Insofar as hardware, the National Instruments Compact R10 Control and Acquisition System can be used, or any other similar system of National Instruments or others can be used.

The scientific cancer cell signal processor 13 includes an electronic communication library/archive of cancer electrical signals obtained from approximately 200 different species of malignant cells. Such signals may be audio or visual and stored/archived. They serve as a baseline data basis to use for reprogramming to develop treatment signals. Also these signals can be compared and altered to function with cancer signals found in patients and stored/archived in the signal processor 13.

The processor 13 also includes a library of potential interfering sounds and signals that would disturb the medical treatment process when using the hybrid computer system. Such interfering signals and sounds must be shielded from the treatment electronics and surgical or treatment field(s). The signals include resident environmental noise and transmissions in the region of the treatment room which may interfere with the sounds and treatment signals. This potential interference includes cell telephone, police radio, television and radio broadcasting frequencies and electrical power line radiation.

Also, human and animal body sounds such as heart and lung sounds along with muscle and digestive noises need to be filtered out so as not to contaminate the treatment signals. These and other waveforms, confounding signals and sounds are incorporated into the computer program/library to use in reprogramming and cleaning up the signals so that only signals that reflect physician selected cellular signals, sounds and waveforms will be available for therapy.

The following definitions apply to the terminology of the present application:

Igniculus signals: The intrinsic operational cellular electrical communication signal, also known as a resident electrical signal, of a cancer cell. Such codes are recorded, studied and re-programmed to develop treatment signals.

Interclusio treatment codes: A treatment communication signal that can stop, confound or pause cancer cell's electrical activity, also known as one form of a confounding electrical signal. Such signal may be pulsed or applied for a calculated period of time to at least damage the cancer cell electrical system to the extent that places the cell on a downward slope toward apoptosis. Used where the malignancy is close to other sensitive structures.

Mortifier Impulus treatment codes: Coded signals that are programmed to cause fatal and irreversible cell death by rapidly destroying the signaling system of a cancer cell cluster to insure the death of the tumor, another form of confounding electrical signal.

Imulus: A treatment tip which is applied directly to a cancer tumor and carries electrical treatment signals via carbon nanotubes or very small metal nanowires. Leads from the scientific computer system 12 connect to the imulus 18. Up to hundreds to thousands of carbon nanotubes 20 may be emplaced on the imulus to transmit the proper treatment code. The imulus may carry and release chemicals and ions into the cell cluster membranes and also inject anti-cancer signals and ions into the cell(s) proper.

Carbon nanotube: Tiny hollow carbon filaments that are about one ten-thousandths the diameter of a human hair. They can be 100 times stronger than steel and able to conduct electricity better than copper. They are meant to touch or pierce the plasma membrane of cancer cells to transmit the treatment signal into the cell processes. As part of their function they can also carry positive or negative ions in the hollow of the nanotube to treat the cell wall glycocalyx to reverse its electrical charge. They are a component of the imulus.

LabVIEW Digital Computer Software: Software manufactured by National Instruments, Version 8 or higher, which is a graphical programming language that uses icons to create applications. It can assimilate libraries of signals and sort to help arrive at the desired final treatment signal. It has capability for processing high speed ultra-low voltage biological signals. This software coupled with the scientific computer system 12 will communicate, record, reprogram and transmit altered cancer cell signals, the confounding electrical signals, designed to damage or destroy cancerous tumors.

For monitoring and pinpointing cancer cells and cancer clusters, research has shown that cancer cells communicate. Therefore, nanotechnology microphones may be designed into the imulus 18 to monitor and pinpoint this communication and aid and/or supplement leading a medical staff to those cancer cells and tumors. The nanotubes 20 can be constructed of a combination of single or double walled carbon nanotubes or nanowires.

The nanotubes can be long tubes of just carbon, but because of the way carbon atoms are bonded together in carbon nanotubes they have unique properties. One of these properties is that they can act as semiconductors, meaning that sometimes they allow electrons to pass through and other times they don't. Both the semiconductor or conductor aspects can be used for therapeutic use.

The installation of the nanotubes or nanowires (arrangement, number, and density) and the control of the imulus 18 is dependent on the treatment needs. The imulus 18 is so small, due to nanotechnology, that a computer aided or robotic control may be required to steady the contact target aim.

Microphones implanted in the imulus 18 represent a key optional component for monitoring the communication between cancer cells The microphones can be utilized to differentiate and pinpoint communication sounds emitted from and between cancer cells and clusters and allow pinpointing cancer cells or clusters for eventful treatment. Also, altered sounds can be part of the treatment modality. The imulus used as a platform for nano-microphones along with nano-lights can be useful to detect small islands of cancer cells by the sounds cancer cells emit when they are heated by light beams. The treatment objective is to disable or destroy every cancer cell that can be located within a patient's body.

While the same imulus 18 can be used for both recording cancer signals and treatment purposes, preferably there are two basic configurations. First is that shown in FIG. 2, which is relatively simple and small. Second is that shown in FIG. 3, where the imulus 22 is larger and more populated with nanotubes or nanowires to achieve a brushlike effect. As discussed above, microphones can be employed in the imulus 22, and also, if needed, a light can be incorporated into the structure. As illustrated, it can have a relatively flat shape, but alternatively can be curved, angled or round in order to optimally accommodate shapes of the malignant tumors 10. A connector 24 is used to connect the imulus 22 to the computer system 12 through the converter 16.

Various features of the invention have been shown and described above. However, it must be understood that what is described herein does not limit but merely illustrates the invention. Various changes can be made to the invention without departing from the spirit thereof or scope of the following claims.

What is claimed:

1. A system for treating cancer by causing apoptosis, comprising
   a. a computer system comprising
      i. a processor for modifying a resident electrical signal found in a specie of cancer to form at least one confounding electrical signal unique to each resident electrical signal, and
      ii. a data storage for all confounding electrical signals, and
   b. a probe for applying a selected one of the confounding electrical signals to the cancer.
2. The system according to claim 1, in which said probe is an imulus.
3. The system according to claim 2, in which the imulus comprises a plurality of nanotubes.
4. The system according to claim 1, in which said computer system includes a hybrid analog computer.
5. The system according to claim 1, including a probe for determining said resident electrical signal.
6. The system according to claim 5, in which said probe includes at least one microphone.
7. The system according to claim 5, in which said probe includes at least one light.
8. The system according to claim 1, including a probe for determining audio signals of the cancer.
9. A system for treating cancer by causing apoptosis, comprising
   a. a first probe for determining a resident electrical signal found in a specie of cancer,
   b. a computer system comprising
      i. a hybrid analog computer,
      ii. a processor for modifying said electrical signal to form at least one confounding electrical signal unique to each resident electrical signal, and
   c. a second probe for applying a selected one of the confounding electrical signals to the cancer.
10. The system according to claim 9, in which said probe is an imulus.
11. The system according to claim 10, in which the imulus comprises a plurality of nanotubes.
12. The system according to claim 9, in which at least one of said probes includes at least one microphone.
13. The system according to claim 9, in which at least one of said probes includes at least one light.
14. The system according to claim 9, in which said probes are the same.
15. A system for treating cancer by causing apoptosis, comprising
   a. a first probe for determining a resident electrical signal found in a specie of cancer,
   b. a computer system comprising
      i. a hybrid analog computer,
      ii. a processor for modifying said electrical signal to form at least one confounding electrical signal unique to each resident electrical signal,
      iii. a data storage for all confounding electrical signals, and
   c. a second probe for applying a selected one of the confounding electrical signals to the cancer.
16. The system according to claim 15, in which said probe is an imulus.
17. The system according to claim 16, in which the imulus comprises a plurality of nanotubes.
18. The system according to claim 15, in which said first probe includes at least one microphone.
19. The system according to claim 15, in which said first probe includes at least one light.
20. The system according to claim 15, including a probe for determining audio signals of the cancer.

* * * * *